United States Patent [19]

Dietz et al.

[11] Patent Number: 5,305,758
[45] Date of Patent: Apr. 26, 1994

[54] ULTRASONIC APPARATUS FOR USE IN OBTAINING BLOOD FLOW INFORMATION

[75] Inventors: Dennis R. Dietz; Lawrence J. Busse, both of Littleton, Colo.

[73] Assignee: Tetrad Corporation, Englewood, Colo.

[21] Appl. No.: 984,717

[22] Filed: Dec. 2, 1992

Related U.S. Application Data

[63] Continuation of Ser. No. 684,221, Apr. 12, 1991, abandoned.

[51] Int. Cl.$^5$ .................................................. A61B 8/12
[52] U.S. Cl. ........................... 128/662.06; 310/313 B
[58] Field of Search ............... 128/661.08, 661.09, 128/662.03, 662.06, 663.01; 310/313 B, 336

[56] References Cited

U.S. PATENT DOCUMENTS

| | | | |
|---|---|---|---|
| 3,760,204 | 9/1973 | Yester, Jr. | 310/313 B |
| 3,792,381 | 2/1974 | Bristol | 310/313 B |
| 4,757,821 | 7/1988 | Snyder | 128/662.06 |
| 4,770,185 | 9/1988 | Silverstein et al. | 128/661.08 |
| 4,920,967 | 5/1990 | Cottonaro et al. | 128/662.06 |
| 4,936,307 | 6/1990 | Saito et al. | 128/662.06 |
| 4,947,852 | 8/1990 | Nassi et al. | 128/662.06 |
| 4,957,112 | 9/1990 | Yokoi et al. | 128/662.06 |
| 5,058,595 | 10/1991 | Kern | 128/662.06 |

*Primary Examiner*—William E. Kamm
*Assistant Examiner*—George Manuel
*Attorney, Agent, or Firm*—Sheridan Ross & McIntosh

[57] ABSTRACT

The present invention provides an apparatus that is useful in obtaining blood flow information. The device includes a carrier that, in preferred embodiments of the invention, includes either a catheter or guide wire. The device further includes at least one transducer that is capable of generating and/or receiving an ultrasonic signal that departs or is received, respectively, by the transducer at an angle to the surface of the transducer that is exposed to the blood flow. One embodiment of the apparatus employs a transducer that is capable of generating a surface acoustic wave (SAW) that, upon contact with blood, is converted into a "leaky" wave. Another embodiment of the device employs a transducer that utilizes the grating lobe effect to transmit and/or receive ultrasonic signals at an angle to the surface of the transducer that is exposed to the blood flow.

7 Claims, 6 Drawing Sheets

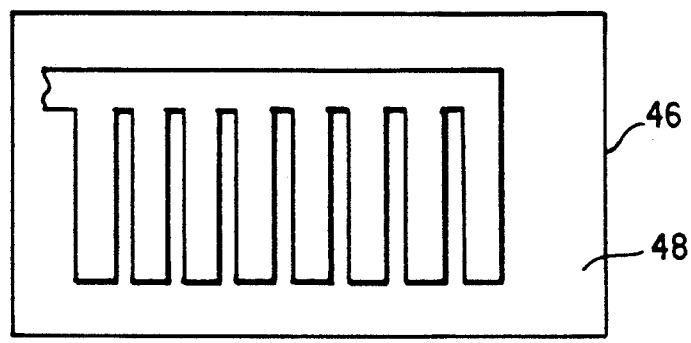
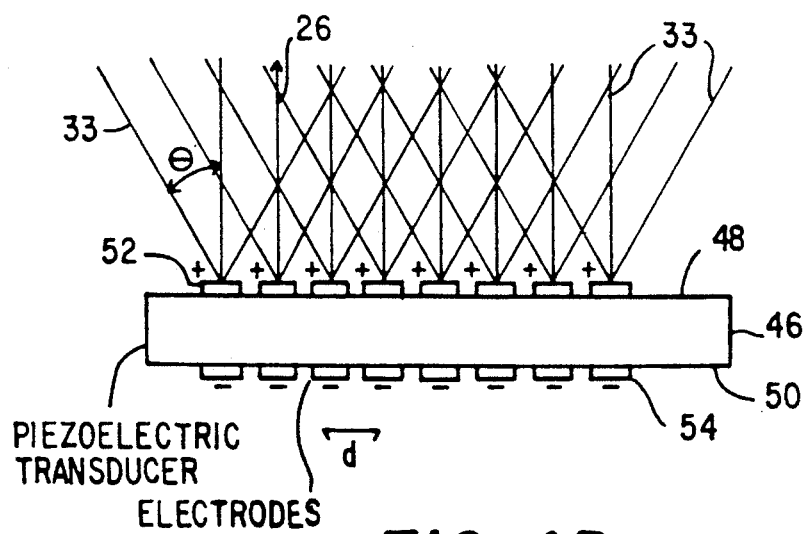

ULTRASONIC APPARATUS FOR USE IN OBTAINING BLOOD FLOW INFORMATION

This is a continuation of co-pending application Ser. No. 07/684,221, filed on Apr. 12, 1991 now abandoned.

BACKGROUND OF THE INVENTION

1. Field of the Invention

The present invention relates to apparatuses that are adapted for use in determining information relating to the flow of blood within a blood vessel, such as blood velocity information and information reflected from the wall of the blood vessel.

2. Description of the Related Art

Vascular disease and, in particular, cardiovascular disease is a major health care problem in the United States that results in over one million deaths per year. Over the last two decades a tremendous amount of research has been conducted on vascular diseases in an effort to identify the causes of such diseases as well as to diagnose and treat such diseases.

Characteristic of many apparatuses used in the diagnosis of vascular diseases and/or in guiding various therapeutic devices used for the treatment of vascular diseases is the use of an ultrasonic device. The ultrasonic device is typically attached to a guide wire or catheter that allows the ultrasonic device to be placed inside a blood vessel or attached to an endoscope, for example, that permits the ultrasonic device to be positioned in a cavity adjacent to the blood vessel of interest. When the apparatus is in operation, the ultrasonic device either generates an ultrasonic signal that interacts with the blood or blood vessel, or receives an ultrasonic signal after it has interacted with the blood or blood vessel and, as a consequence, now possesses information relating to the blood or blood vessel. Among the information that the ultrasonic device can be used to obtain are information on the vessel lumen or wall as well as hemodynamic measurements, such as blood velocity. To obtain blood velocity information and other related information, the ultrasonic device must be capable of generating or receiving an ultrasonic signal where at least one component of a vector representative of the direction of propagation of the ultrasonic signal is substantially parallel to the direction in which the blood is flowing. The vector representative of the direction of propagation of a plane ultrasonic wave that is generated or received by the ultrasonic device is a vector that is substantially perpendicular to the wave fronts of the plane ultrasonic wave. For non-planar ultrasonic waves that are generated by the ultrasonic device, such as concentric waves, the vector representative of the direction of propagation of the non-planar ultrasonic wave is a vector that is substantially perpendicular to the wave fronts as well as substantially centered in the angular extent over which the wave propagates or indicative of the direction in which the greatest signal strength lies. The vector representative of the direction of propagation of a non-planar ultrasonic wave that is received by the ultrasonic device is a vector that is substantially perpendicular to the wave fronts. Hereinafter, the vector representative of the direction of propagation of an ultrasonic signal will be referred to as the directional vector.

One known apparatus that has been proposed for transmitting or receiving an ultrasonic signal where at least one component of its directional vector is substantially parallel to the direction of blood flow includes a guide wire or catheter with a piezoelectric transducer positioned on the tip of the guide wire or catheter such that the area vector of the transducer, a vector that is perpendicular to the surface of the transducer from which an ultrasonic wave emanates or upon which an ultrasonic wave impinges, is substantially parallel to the direction of blood flow when the apparatus is in use. In operation, the piezoelectric transducer transmits or receives ultrasonic signals having directional vectors that are substantially parallel to the area vector of the transducer and, as a consequence, substantially parallel to the direction of blood flow. An example of such an apparatus is shown in U.S. Pat. No. 4,920,967, which issued on May 1, 1990, to Cottonaro et al., and is entitled "Doppler Tip Wire Guide". Under ideal conditions, the apparatus is inserted into a blood vessel and the piezoelectric transducer is pulsed to produce an ultrasonic signal having a directional vector that is substantially parallel to the area vector of the piezoelectric transducer and, as a consequence, the direction of blood flow. The blood reflects the ultrasonic signal and in so doing Doppler shifts the frequency of the ultrasonic signal by an amount that is indicative of the velocity at which the blood is flowing. The portion of the reflected signal that has a directional vector that is substantially parallel to the area vector of the transducer is then detected by the piezoelectric transducer and converted into an electrical signal that can be processed to determine the blood velocity. There are several drawbacks associated with this apparatus. Namely, the tip of the catheter or guide wire and the piezoelectric transducer in many instances tend to rest against the wall of the blood vessel. As a consequence, the ultrasonic signal transmitted or received by the piezoelectric transducer is corrupted by the vessel wall and therefore does not result in a very reliable indication of the blood flow velocity or related parameter. Moreover, in order to produce an ultrasonic signal having sufficient power to obtain reliable blood flow information, the frontal surface area of the piezoelectric transducer must be relatively large. This large surface area, however, inhibits the placement of the piezoelectric transducer in small diameter vessels, some of which, and especially in the case of the myocardium, are quite important.

Another known apparatus that has been proposed for transmitting or receiving ultrasonic signals having directional vectors with a component parallel to the direction in which the blood is flowing includes a catheter or guide wire with a piezoelectric transducer located on the side of the catheter or guide wire and at an angle to the longitudinal axis of the catheter or guide wire. An example of such an apparatus is shown in U.S. Pat. No. 4,770,185 ('185), which issued on Sept. 13, 1988, to Silverstein et al., and is entitled "Method and Apparatus for Endoscopic Blood Flow Detection By The Use of Ultrasonic Energy." Another example of such a device is shown in U.S. Pat. No. 4,947,852 ('852), which issued on Aug. 14, 1990, to Nassi et al., is entitled "Apparatus and Method for Continuously Measuring Volumetric Blood Flow Using Multiple Transducers and Catheter for Use Therewith". The piezoelectric transducer can be planar, as shown in FIG. 3 of the '852 patent, or frusto-conical, as shown in FIG. 14 of the '185 patent. In either case, when the apparatus is in use, the piezoelectric transducer generates or receives ultrasonic signals having directional vectors that are substantially parallel to the area vector of the piezoelectric transducer. Since the transducer is angled with respect to the longitudinal axis of the catheter or guide wire and the longitudinal axis is substantially parallel to the direction of blood flow when the apparatus is in use, the directional vector of the ultrasonic signals generated by the piezoelectric transducer are at an angle to the direction of blood flow. Similarly, the directional vector of the ultrasonic signals that the piezoelectric transducer can receive are at angle to the direction of blood flow. Since the directional vectors of the transmitted or received ultrasonic signals are at an angle to the direction of blood flow, a component of the directional vectors is also substantially parallel to the direction of blood flow and, as such, can be used to determine blood velocity and related information. This type of apparatus also has several drawbacks. Specifically, the overall diameter or thickness of the apparatus increases as the angle of the transducer with respect to the longitudinal axis of the guide wire or catheter increases. This, in turn, reduces the ability of the device to be placed in small diameter vessels, many of which, as previously mentioned, can be quite important. Moreover, placing the piezoelectric transducer at an angle to the longitudinal axis of the catheter or guide wire requires that an appropriately angled mounting surface be fabricated or in some other way machined on the catheter or guide wire. This, in turn, adds to the complexity and, in all likelihood, the cost of producing such an apparatus.

Yet another known apparatus that has been proposed for use in determining blood velocity and related information using an ultrasonic signal includes a catheter or guide wire with a piezoelectric transducer located on the side of the catheter or guide wire with the area vector of the piezoelectric transducer oriented such that it is substantially parallel to the longitudinal axis of the catheter or guide wire. Positioned adjacent to the piezoelectric transducer is a reflector that reflects any ultrasonic signal produced by the piezoelectric transducer such that the directional vector of the reflected ultrasonic signal is at an angle to the longitudinal axis of the catheter or guide wire, which is also at an angle to the direction of blood flow when the apparatus is in use. Conversely, the reflector reflects ultrasonic signals that impinge upon it at an angle to the longitudinal axis of the catheter, or at an angle the direction of blood flow when in use, so that the directional vector of the reflected ultrasonic signal impinges upon the piezoelectric transducer from a direction that is substantially parallel to the area vector of the piezoelectric transducer. Since the directional vectors of the ultrasonic signals that the reflector receives from the blood or reflects into the blood are at an angle to the direction of blood flow, there is a component of the ultrasonic signals that is substantially parallel to the direction of blood flow that can be used to determine blood velocity and related information. An example of such a device is shown in U.S. Pat. No. 4,757,821, which issued on Jul. 19, 1988, to Snyder and is entitled "Omnidirectional Ultrasonic Probe". Due to the orientation of the piezoelectric transducers and reflective structures, this type of apparatus possesses a relatively large diameter that prevents this type of apparatus from being maneuvered into small diameter blood vessels. Moreover, the need to fabricate reflective surfaces and properly orient the piezoelectric transducer with respect to such surfaces makes this type of apparatus difficult to build and, as a consequence, more expensive.

Another known device that has been proposed for use in determining blood flow information using an ultrasonic signal is shown in FIG. 11 of the '852 patent. The device includes a catheter or guidewire with an ultrasonic transducer that, due to either its curved surface, narrow dimension, or its coupling with an acoustic lens is apparently capable of receiving ultrasonic signals having directional vectors that extend over a range of angles. The use of a transducer with a curved surface, another example of which is shown in FIGS. 10A and 10B of the '185 reference, is apparently capable of receiving ultrasonic signals having directional vectors that extend over a range of angles with respect to the longitudinal axis of the catheter or guidewire. This ability is apparently due to the curved surface having a plurality of surface area vectors that extend over the relevant range. Consequently, if the directional vector of an ultrasonic signal that impinges upon the transducer is substantially parallel with the surface area vector of the transducer at the point where it impinges upon the transducer, then the transducer will convert the ultrasonic signal into an electrical signal. This type of transducer is not sensitive to signals that impinge upon it at an angle to the surface area vector at the point of impact. A drawback associated with using a transducer with a curved surface is that the curved surface increases the overall diameter of the device in much the same manner as the devices that utilize a transducer set at an angle to the longitudinal axis of the guide wire or catheter. The relatively large diameter of such a device, as previously mentioned, is undesirable in many instances.

The narrow dimension transducer, at least functionally, also has a plurality of surface area vectors and, as a consequence, is apparently capable of receiving ultrasonic signals over a range of angles. However, such a transducer does not appear to be able to receive an ultrasonic signal that impinges upon it that has a directional vector that is at an angle to one of the plurality of surface area vectors. Such sensitivity is achieved by using a narrow dimension transducer with a plurality of surface area vectors going in different directions. Consequently, even though the transducer is of narrow dimension, it must be oriented to capture ultrasonic signals over the range of interest. This, in turn, results in the ultrasonic transducer contributing to the overall diameter of the device and thereby reducing the ability of the device to be used in small diameter blood vessels.

The apparent purpose of the acoustic lens is to bend or divert ultrasonic signals with directional vectors that impinge upon it over a range of angles with respect to the surface area vector of the ultrasonic transducer such that the directional vector of the ultrasonic signal when it departs the acoustic lens is substantially perpendicular to the surface area vector of the transducer. This, in turn, allows the transducer to detect the ultrasonic signal and convert the ultrasonic signal into an electrical signal. Moreover, the use of a lens, if placed on the side of a catheter or guide wire, increases the overall diameter of the device which, in turn, limits the diameter of blood vessels within which such a device can be positioned. In addition, the use of an acoustic lens, as with the devices that use a reflector, makes the device more difficult to build and, in all likelihood, more expensive.

The '852 patent also shows in FIG. 10 a pair of transducers that are used to measure the distance between the catheter and the wall of the blood vessel. The transducers used in the '852 patent appear to generate or receive ultrasonic waves that have directional vectors that are parallel to the surface area vector of the ultrasonic transducer. When a wave pattern is generated where the wave fronts are non-parallel, as in a wave pattern where the wave fronts are concentric, and form a fan-like pattern similar to lobe of the signal associated with an antenna, the directional vector is considered herein to be the vector that is substantially centered in the wave pattern. Consequently, the direction of wave propagation of the ultrasonic signal generated by the ultrasonic transducer $T_3$ that is shown in FIG. 10 of the '852 patent is not believed to be indicative of the directional vector of the ultrasonic wave as defined herein, but merely to indicate that the transducer generates ultrasonic signals having non-parallel or concentric wave fronts that can be used to perform the required distance measurement. Similar statements can be made with respect to the ultrasonic signal received by the ultrasonic transducer $T_4$. Consequently, the transducers $T_3$ and $T_4$ shown in the '852 reference are not believed to be capable of generating or receiving, respectively, ultrasonic signals with directional vectors that are at angles to the surface area vectors of the transducers $T_3$ and $T_4$, respectively.

Based on the foregoing, there is a need for an ultrasonic apparatus for obtaining hemodynamic information, such as blood flow velocity, that addresses the drawbacks associated with the presently known ultrasonic apparatuses for obtaining such information. More specifically, there is a need for a device for obtaining hemodynamic information that is capable of transmitting or receiving ultrasonic signals at an angle to the surface area vector of the ultrasonic transducer employed in the device. This, in turn, would allow a device having a relatively small thickness or diameter to be realized that would, in turn, allow the device to be placed in blood vessels or orifices adjacent to a blood vessel having correspondingly small diameters. In addition, there is a need for an ultrasonic apparatus for obtaining hemodynamic information that has a reduced number of components relative to many of the known apparatuses for obtaining hemodynamic information, and, as a consequence, is easier and less expensive to manufacture.

SUMMARY OF THE INVENTION

The present invention provides an apparatus for use in obtaining information relating to the flow of blood within a vessel. Typical of the type of information that the apparatus can be used to obtain are the mean or average blood velocity, a transverse or longitudinal blood velocity profile, blood volume per unit of time, and ultrasound signals reflected from the vessel wall.

The invention includes a carrier having a surface on which a device for generating or receiving an ultrasonic signal, which will hereinafter be referred to as the ultrasonic device, is located. The ultrasonic device has a surface from which an ultrasonic signal emanates or onto which an ultrasonic signal can impinge when the ultrasonic device is being used to generate or receive, respectively, an ultrasonic signal. Unlike the known ultrasonic apparatuses, however, the ultrasonic apparatus of the present invention operates such that the ultrasonic signal, whether generated or received, is communicated at an angle to the area vector of the surface of the ultrasonic device. Consequently, if the ultrasonic device is located on the side of a catheter or guide wire, there is no need in the present invention to position the ultrasonic device at an angle to the direction of blood flow, as in the '185 patent, or to construct intervening devices such as mirrors or acoustic lenses between the surface of the ultrasonic apparatus and the blood, as in the '821 patent. Moreover, there is no need to use a curved surface transducer, as in the '852 patent, that adds to the overall thickness of the device nor is there a need to use a narrow dimension transducer, as in the '852 patent. This, in turn, also results in an apparatus that is simpler and, as a consequence, easier and less expensive to manufacture. Moreover, the overall thickness or diameter of the apparatus, i.e., the carrier in combination with the ultrasonic device, is considerably less than many of the known apparatuses for performing hemodynamic measurements. Consequently, the apparatus can be positioned in much smaller blood vessels or cavities adjacent to blood vessels.

In certain embodiments of the invention, the carrier is either a catheter or guide wire that is used to position the ultrasonic device within the blood vessel when in use. However, the carrier can also be an endoscope or similar device that positions the ultrasonic device in an cavity that is exterior to, but substantially adjacent to, the blood vessel of interest. It is further believed that the carrier can, in the appropriate circumstances, be a structure that is applied to the dermis or skin to position the ultrasonic device adjacent to the appropriate blood vessel.

In one embodiment of the invention, the ultrasonic device is capable of generating a surface acoustic wave (SAW) that, when it comes into contact with blood, is converted into at least one longitudinal "Leaky" wave that has a directional vector that is at an angle to the area vector of the device. Another embodiment of the invention employs an ultrasonic device that operates based on grating lobe principles to produce a bulk wave that has a directional vector that is at an angle to the area vector of the device and/or receives ultrasonic signals having directional vectors at a comparable angle.

In embodiments of the invention that employ a catheter or guide wire as the carrier, the ultrasonic device can be shaped such that off-axis sensitivity is obtained, which is useful in determining blood velocity information, for example. Typically, such a device is planar in shape. Alternatively, the ultrasonic device can be shaped so as to surround the catheter or guide wire and thereby be used to obtain conical beam sensitivity, which is useful in obtaining transverse blood velocity profiles, for example. Typically, such a device is cylindrical in shape.

In other embodiments of the invention, a second ultrasonic device is located on the carrier and used in conjunction with the first ultrasonic device to, for example, obtain a longitudinal or transverse velocity profile, which can be used, for example, to pinpoint obstructions or constrictions within a vessel.

Based on the foregoing, the present invention provides an apparatus that is useful in obtaining hemodynamic blood flow data and presents several advantages with respect to known ultrasonic apparatuses for obtaining such measurements. Specifically, the present invention provides an apparatus that is capable of communicating ultrasonic signals having directional vectors that are at an angle to the surface area vectors of the transducers employed in the apparatus. As a consequence, the device of the present invention can exhibit reduced dimensional characteristics with respect to many of the known ultrasonic apparatuses for performing hemodynamic blood flow measurements. This reduced dimensional aspect allows the device to be placed in smaller blood vessels or cavities adjacent to the blood vessel of interest than presently known ultrasonic apparatuses are capable of being positioned within. Moreover, the present invention requires substantially fewer parts or structures than many of the presently known ultrasonic apparatuses for use in blood flow measurements. Consequently, the present invention is simpler, easier, and less expensive to fabricate or construct relative to known ultrasonic apparatuses.

BRIEF DESCRIPTION OF THE DRAWINGS

FIGS. 4A-4B illustrate a substantially planar, grating lobe piezoelectric device that can be used with the embodiment of the invention illustrated in FIGS. 1A-1C and is capable of generating a bulk wave;

DESCRIPTION OF THE PREFERRED EMBODIMENTS

Figure 1A:
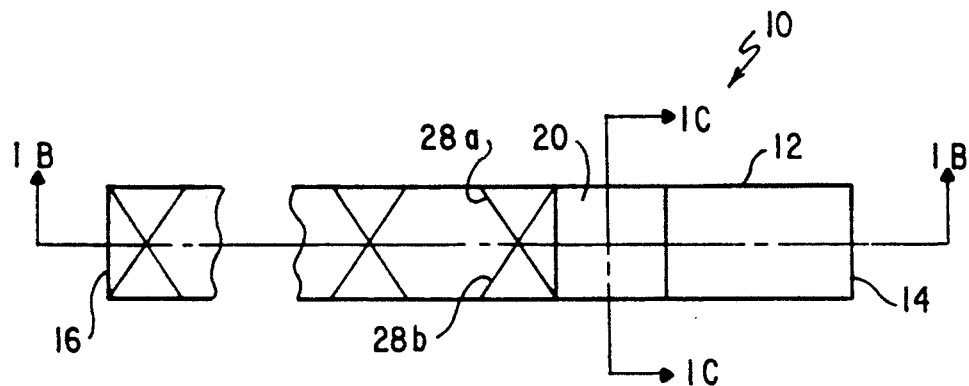
FIGS. 1A-1C illustrate an embodiment of the invention that utilizes a substantially planar ultrasonic device.
Figure 1B:
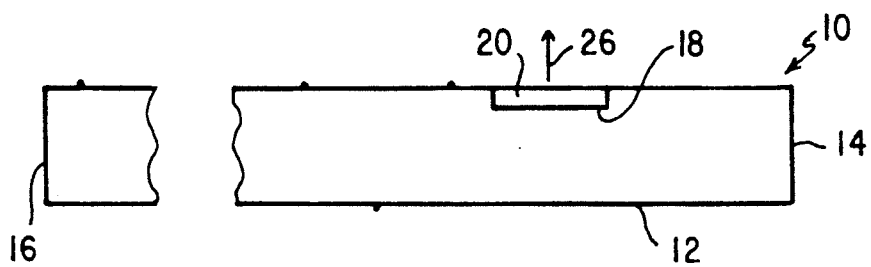
Figure 1C:
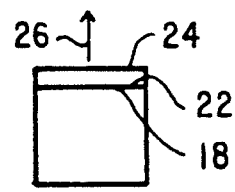

With reference to FIGS. 1A-1C, one embodiment of the apparatus for use in determining information relating to the flow of blood within a blood vessel 10, hereinafter referred to as apparatus 10, is illustrated. Among the types of information relating to the flow of blood within a blood vessel that the apparatus is capable of being used to obtain include the mean or average blood velocity, a longitudinal or transverse velocity profile, information relating to the wall or lumen of the blood vessel, and the diameter of the blood vessel.

The apparatus 10 includes a carrier 12 having a first terminal end 14 and a second terminal end 16. Located intermediate the first terminal end 14 and the second terminal end 16 of the carrier 12 is a mounting surface 18 for an ultrasonic device. The carrier 12 can be a catheter or guide wire that is suitably dimensioned for insertion into a blood vessel. For example, a suitably dimensioned guide wire is approximately 2 to 3 feet in length and has a thickness or diameter of 0.014 to 0.040 of an inch. Typically, a guide wire is made of a substantially, biologically inert material such as stainless steel or titanium. In contrast, the thickness or diameter of catheters typically range from less than one millimeter to several millimeters. Generally, catheters are made from extruded plastics, which are also substantially, biologically inert. The materials used to realize catheters and guidewires are also, generally, quite flexible so that the guidewire or catheter can follow the path of the blood vessel in which it is inserted when in use. The carrier 12 can also be an endoscope that is suitably dimensioned and made of the appropriate materials for insertion into a cavity that is adjacent to the blood vessel of interest. Additionally, the carrier can be a structure that is appropriately configured for application to the skin or dermis substantially adjacent to the blood vessel of interest.

The apparatus 10 further includes an ultrasonic device 20 for use in generating an ultrasonic signal that propagates through the blood in a blood vessel or receiving an ultrasonic signal after the ultrasonic signal has interacted with the blood in a blood vessel and/or the wall or lumen of the blood vessel. Preferably, the ultrasonic signals are in the form of plane waves where the wave fronts are substantially parallel to one another and the direction in which the wave is propagating can be represented by a directional vector that is normal to the wave fronts. For ultrasonic signals that exhibit non-planar wave fronts and are generated by the ultrasonic device 20, the direction in which the wave is propagating can be represented by a directional vector that is substantially perpendicular to the wave fronts and traverses a path substantially in the center of the wave pattern or traverses the path of greatest signal strength. For ultrasonic signals that exhibit non-planar wave fronts and are received by the ultrasonic device 20, the directional vector is substantially perpendicular to the wave fronts. The ultrasonic device 20 includes a lower surface 22 for interfacing with the mounting surface 18 of the carrier 12. The ultrasonic device also has an upper surface 24 from which an ultrasonic signal emanates or onto which an ultrasonic signal impinges when the ultrasonic device is being used to generate or receive an ultrasonic signal, respectively. The upper surface 24 has an area vector 26, which is a vector that is substantially perpendicular to a point on the upper surface 24. A first lead 28a and a second lead 28b connect the ultrasonic device 20 to circuitry (not shown) that drives the ultrasonic device 20 during the generation of an ultrasonic signal or receives the electrical signal produced by the ultrasonic device 20 when it receives an ultrasonic signal. The ultrasonic device 20 can be a piezoelectric transducer or a piezoelectric transducer attached to a semiconductor substrate that is, in turn, bonded to the carrier 12. In some cases, the piezoelectic transducer is established on the carrier 12 using chemical deposition, vapor deposition, plasma deposition or sputtering techniques. The first and second leads 28a, 28b, are either fine wires or deposited metal film electrodes.

Figure 2:
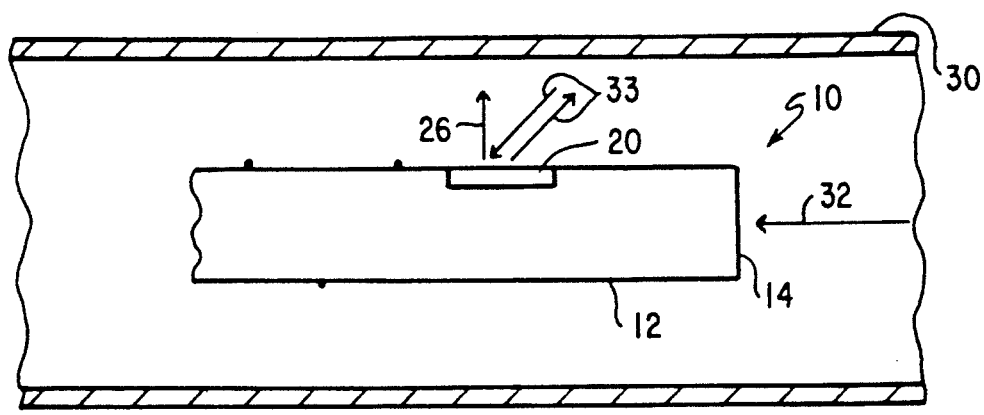
FIG. 2 illustrates, in cross-section, the use of the embodiment of the invention illustrated in FIGS. 1A-1C in determining the velocity of blood in a blood vessel.

With reference to FIG. 2, the use of the apparatus 10 in generating or receiving an ultrasonic signal when the apparatus 10 is positioned within a blood vessel 30 (the carrier 12 in this case is either a catheter o guide wire)

is illustrated. The direction that blood is flowing within the blood vessel 30 is represented by vector 32. When the apparatus 10 is in operation, ultrasonic signals are communicated between the ultrasonic device 20 and the blood or wall of the blood vessel such that a component of the vector representing the direction in which the ultrasonic signals are being communicated, directional vector 33, is at an angle to both the area vector 26 and the vector 32. It is this ability to communicate ultrasonic signals having directional vectors 33 that are at an angle to the area vector 26 that allows the ultrasonic device 20 to be positioned intermediate the first terminal end 14 and the second terminal end 16 of the carrier 12 and be used to obtain information relating to the blood velocity, due to directional vector 33 of the ultrasonic signal being at an angle to the vector 32 of the blood. This, in turn, allows the apparatus to realize a reduced thickness relative to known ultrasonic apparatuses for obtaining blood flow information. Known ultrasonic apparatuses that position an ultrasonic device intermediate to the terminal ends of, for example, a catheter or guide wire such that area vector of the ultrasonic device is parallel to or at an angle to the direction of blood flow exhibit a thickness or diameter that prevents their insertion into small diameter blood vessels. The reduced thickness of the apparatus 10, in contrast, allows the apparatus 10 to be inserted into blood vessels or cavities that are considerably smaller than those into which the known apparatuses can be inserted.

The ultrasonic device 20 can also be positioned on the first terminal end 14 of the carrier 12 such that the area vector 26 is substantially parallel to the vector 32 representative of the direction of blood flow when the apparatus 10 is in use. Locating the ultrasonic device 20 on the first terminal end 14 does, however, diminish the ability of the apparatus 10 to be positioned in smaller blood vessels or orifices than presently known apparatuses for obtaining blood flow information. When the apparatus 10 is in operation, ultrasonic signals are communicated between the ultrasonic device 20 and the blood or wall of the blood vessel such that the directional vectors of the ultrasonic signals are at an angle to the area vector 26

Figure 3A:
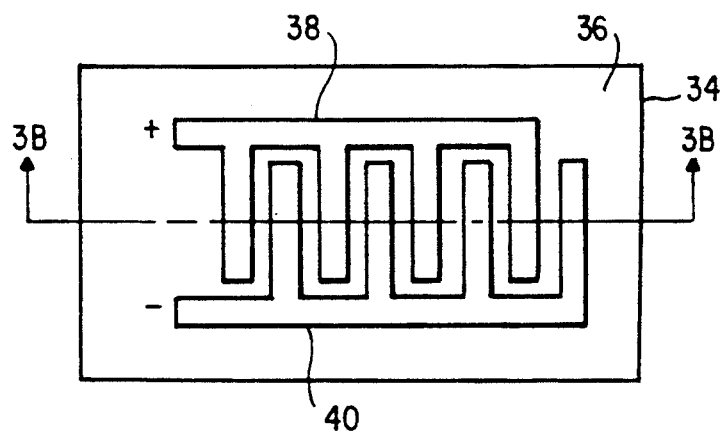
FIGS. 3A-3B illustrate a substantially planar, interdigital piezoelectric device that can be used in the embodiment of the invention illustrated in 1A-1C and is capable of generating a surface acoustic wave (SAW)
Figure 3B:
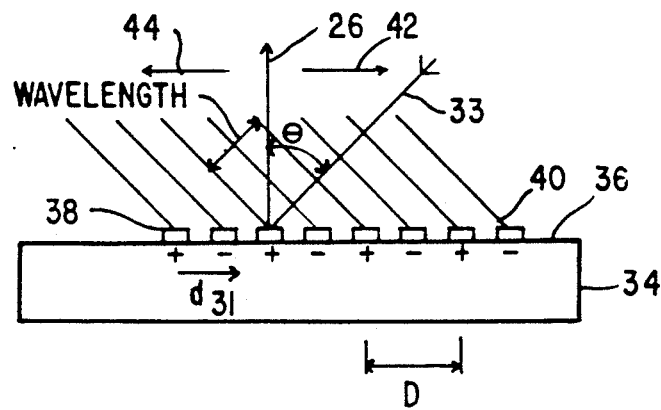

With reference to FIGS. 3A-3B, one type of ultrasonic device 20 that is capable of directly communicating ultrasonic signals at an angle, as previously defined, to the area vector 26 when the apparatus is in use is illustrated. The ultrasonic device 20 includes a piezoelectric plate 34 that is poled at an arbitrary angle to the area vector 26, but typically poled substantially parallel to the area vector 26. The piezoelectric plate 34 has a lower surface 22 that is operatively connected to the mounting surface 18 of the carrier 12. The piezoelectric plate 34 also has an outer surface 36. Located on the outer surface are a positive electrode 38 and a negative electrode 40 that each include "fingers" that interlock with the "fingers" of the other to form an interdigital pattern. The outer surface 36 in combination with the positive electrode 3 and the negative electrode 40 form the upper surface 24 of the ultrasonic device 20. When this type of ultrasonic device 20 is excited by the application of an electrical signal to the positive electrode 38 and the negative electrode 40, a pair of surface acoustic waves (SAW), which are also known as a Raleigh waves, are generated on the outer surface 36 of the piezoelectric plate 34. One of the surface acoustic waves propagates in the positive direction 42 and the other propagates in the negative direction 44. The wave length of the surface acoustic wave is equal to the spacing between the "fingers" comprising either the positive electrode 38 or the negative electrode 40. Since the outer surface 36 of the piezoelectric plate 34 is in contact with the blood within the blood vessel or some other fluid, the surface acoustic waves are immediately converted into ultrasonic, bulk waves that have directional vectors 33 that are at angles $\pm\Theta$ with respect to the area vector 26. This mode of wave propagation is typically termed a "leaky wave". The relationship between the wave length of the "leaky waves" and the angle of propagation is represented by the following equation:

$$\lambda = D \sin(\Theta) \quad (1)$$

where $\lambda$ is the wavelength of the "leaky" waves and "D" is the distance between the "fingers" comprising either the positive electrode 38 or the negative electrode 40. Incidentally, as the number of "fingers" that comprise the positive electrode 38 and the negative electrode 40 increase, the ultrasonic wave that the ultrasonic device 20 is capable of generating becomes more planar. When the ultrasonic device 20 is used to receive ultrasonic signals that impinge upon the piezoelectric plate 34 at angles $\pm\Theta$, Rayleigh waves are generated that, in turn, establish electrical fields that are substantially tangential to the outer surface 36. Due to these electrical fields, a current is induced in the positive electrode 38 and the negative electrode 40 that can be used to ascertain the required information regarding blood flow within the blood vessel.

FIGS. 4A and 4B illustrate another type ultrasonic device 20 that can be used to communicate an ultrasonic signal with a directional vector that is at an angle to the area vector 26. In contrast to the previously mentioned type of ultrasonic device 20 that is capable of producing a SAW, this type of ultrasonic device 20 communicates ultrasonic information at an angle based on grating lobe principles. This type of ultrasonic device 20 includes a thickness mode piezoelectric plate 46, which will hereinafter be referred to piezoelectric plate 46. The piezoeleotric plate 46 includes a first surface 48 and a second surface 50. Located on the first surface 48 are a plurality of positive electrodes 52. A corresponding plurality of negative electrodes 54 are located on the second surface 50. The second surface 50 and the negative electrodes 54 comprise the lower surface 22 of the ultrasonic device 20 that is operatively attached to the mounting surface 18 of the carrier 12. The first surface 48 and the positive electrodes 52 comprise the upper surface 24 of the ultrasonic device 20. By placing the positive electrodes 52 at an interval that is greater than $\lambda/2$ (where $\lambda$ is the wavelength of the ultrasonic signal), ultrasonic, bulk signals that have directional vectors that are at angles $\pm\Theta$ as well as zero degrees relative to the area vector 26 can be produced by applying the appropriate signal to the piezoelectric plate 46 using the positive electrode 52 and the negative electrode 54. Conversely, when this type of ultrasonic device 20 is used to receive ultrasonic signals, it is sensitive to ultrasonic signals that impinge upon the first surface 48 at these angles, i.e. a current is induced in the positive and negative electrodes 52, 54, that is representative of the ultrasonic signals that impinge upon the first surface 48 of the ultrasonic device 20 at these angles. In essence, this type of ultrasonic device 20 forms a diffraction grating where the relationship between the wavelength λ and angle Θ is represented by the Bragg diffraction equation:

$$n\lambda = d \sin(\Theta) \qquad (2)$$

where "n" is the diffraction order and "d" is the spacing between the positive electrodes 52 or the negative electrodes 54. It should be noted, however, that the negative electrode 54 can be replaced with a single electrode that extends the length of the positive electrode 52 if desired. Moreover, as the number of "fingers" that comprise the electrode located on the first surface 48 increases, the ultrasonic wave that the ultrasonic device 20 is capable of generating becomes more planar.

Figure 5A:
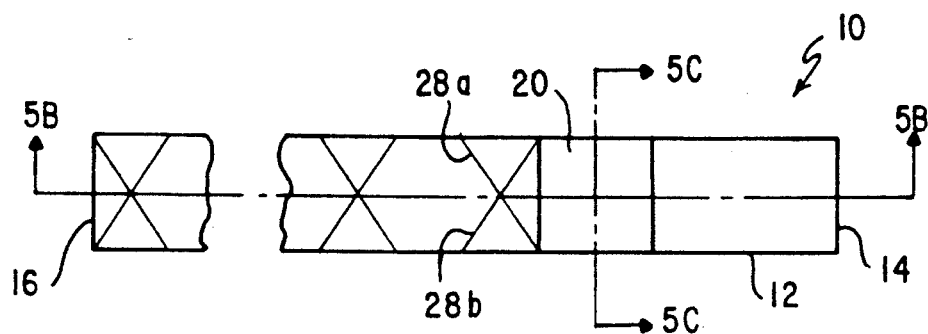
FIGS. 5A-5C illustrate another embodiment of the invention where the ultrasonic device is substantially cylindrical so as to provide conical beam sensitivity.
Figure 5B:
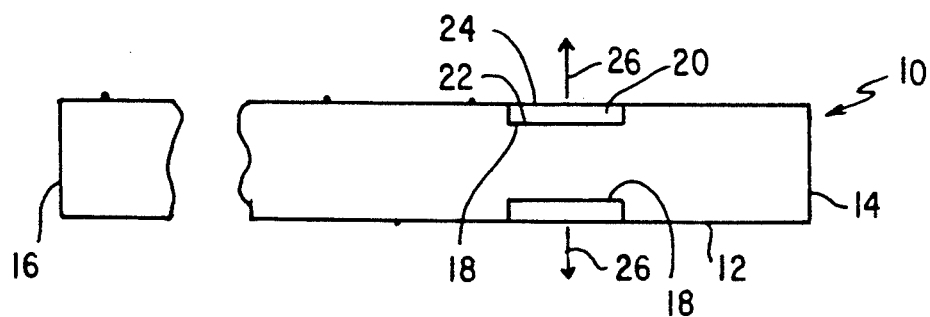
Figure 5C:
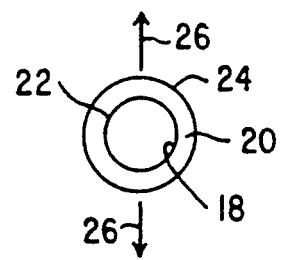
Figure 6:
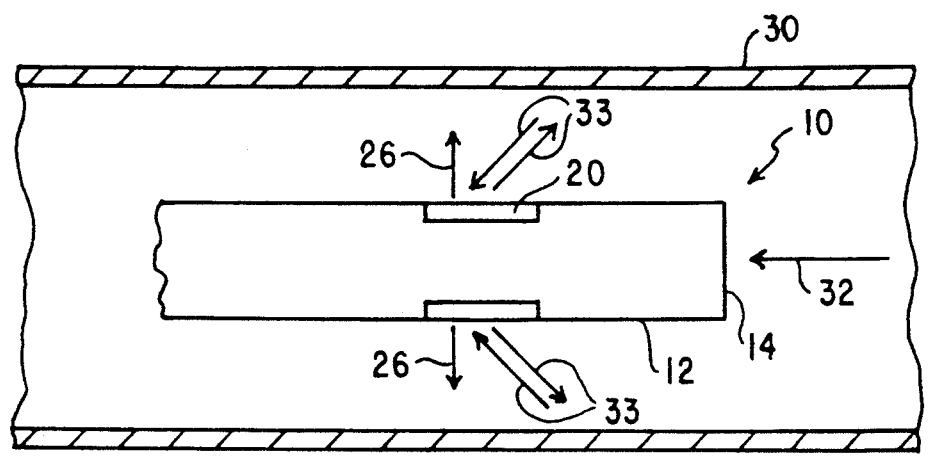
FIG. 6 illustrates, in cross-section, the use of the embodiment of the invention illustrated in FIG. 5 to measure the velocity of blood in a blood vessel.
Figure 9:
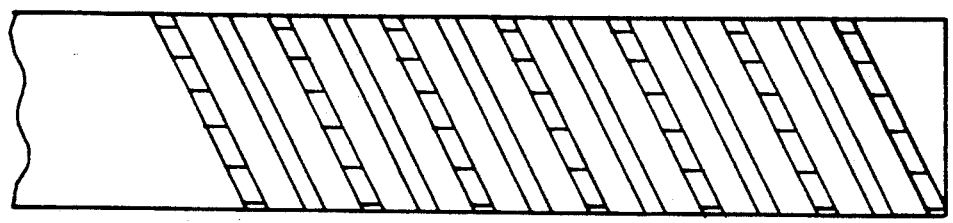
FIG. 9 illustrates an ultrasonic device in which two electrodes associated with the ultrasonic device are established in a double helix pattern.
Figure 10:
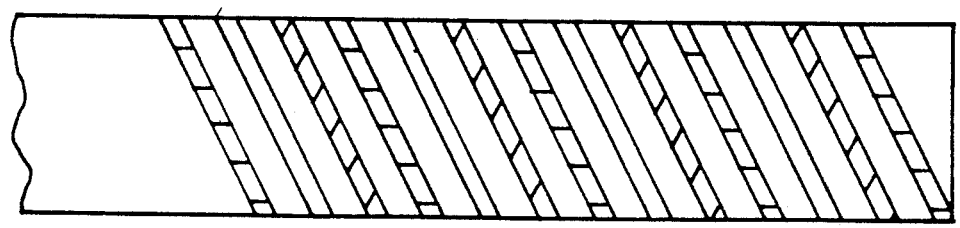
FIG. 10 illustrates an ultrasonic device in which three electrodes associated with the ultrasonic device are established in a triple helix pattern.

With reference to FIGS. 5A-5C, an embodiment of the apparatus 10 that is capable of conical beam sensitivity is illustrated. The ultrasonic device 20, in contrast to the flat ultrasonic device 20 illustrated in FIGS. 1A-1C, 2A-2B, and 3A-3B, forms a continuous surface that closes upon itself. In the illustrated embodiment, the continuous surface that closes upon itself is a cylinder. Other continuous surfaces are, however, feasible. Either of the types of ultrasonic device 20 illustrated in FIGS. 2 or 3 can be used in this particular embodiment of the apparatus 10. If the type of ultrasonic device 20 illustrated in FIGS. 2A-2B is utilized, the positive electrode 38 and negative electrode 40 can be formed by etching a double helix or double screw pattern on the surface of the piezoelectric plate 34, as illustrated in FIG. 9. Providing that the pitch of each helix is relatively high, the double helix pattern will perform very much like a series of parallel rings around the circumference of the piezoelectric plate 34. This eliminates the need for electrical interconnections from ring to ring. By adding a third helix, as illustrated in FIG. 10, single angle sensitivity can be achieved by phasing the electrical signals between the three electrodes so as to eliminate sensitivity to one of the surface acoustic waves. FIG. 6 illustrates this embodiment of the apparatus 10 being used to generate a conical, ultrasonic signal and/or receive a conical ultrasonic signal that can, for example, be used to determine the volume of blood flow.

Figure 7:
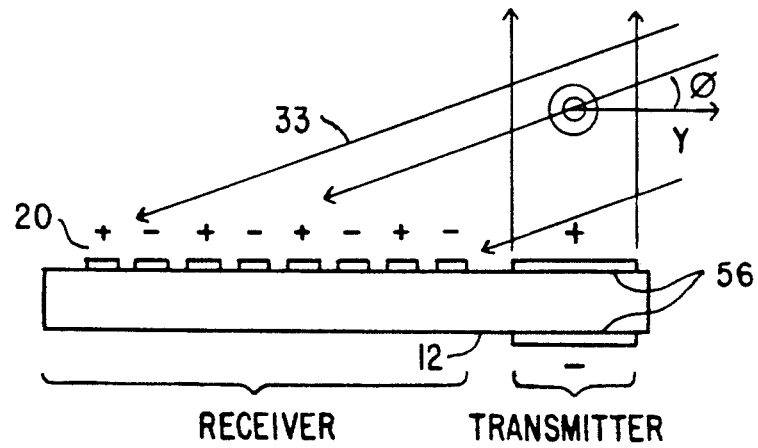
FIG. 7 illustrates an embodiment of the invention where the ultrasonic device illustrated in FIG. 1 is used as a receiver and a second ultrasonic device that produces an ultrasonic signal that is substantially parallel to its area vector is used as a transmitter to obtain blood velocity profile information.

With reference to FIG. 7, a further embodiment of the apparatus 10 is illustrated. This embodiment of the apparatus 10 employs a second ultrasonic device 56 that is capable of transmitting an ultrasonic signal substantially parallel to its area vector as a transmitter and the type of ultrasonic device 20 illustrated in FIGS. 3A-3B as a receiver (the type of ultrasonic device 20 illustrated in FIGS. 4A-4B can also be employed). Since there are separate ultrasonic devices for transmitting and receiving this embodiment is capable of operating in a pulsed mode or a continuous mode where the second ultrasonic device 56 is continually generating an ultrasonic signal and the ultrasonic device 20 is continually receiving the ultrasonic signal that results from the interaction of the transmitted ultrasonic signal with the blood or blood vessel wall. In contrast, the embodiments of the apparatus 10 that employ a single ultrasonic device 20 to transmit and receive are operated in a pulse mode where, alternatingly, the ultrasonic device generates an ultrasonic signal for a defined time, and then ceases operation so that any returning ultrasonic can be detected. The embodiment of the apparatus 10 illustrated in FIG. 7 can be used to obtain a transverse blood velocity profile by appropriately sampling the ultrasonic signal received by the ultrasonic device 20 as well as to make volume flow measurements. Planar embodiments of the ultrasonic device 20 or ultrasonic devices shaped so as to form a continuous surface that closes upon itself can be employed to obtain off-axis beam sensitivity or conical beam sensitivity, respectively. Moreover, either of the types of ultrasonic device 20 illustrated in FIGS. 2 or 3 can be employed for the receiver portion of the apparatus 10. Preferably, a thickness mode piezoelectric transducer is employed as the second ultrasonic device 56.

When the embodiment of the apparatus 10 that is illustrated in FIG. 7 is in operation, the second ultrasonic device 56 produces an ultrasonic signal having a directional vector that is parallel to its area vector and that interacts with constituents within the blood stream. These constituents, upon being radiated with the ultrasonic signal, re-radiate or reflect the ultrasonic signal in several different directions. The ultrasonic device 20 is sensitive to the portion of the re-radiated ultrasonic signal that impinges upon it at the angle, with the respect to the area vector 26, to which it is sensitive. The ultrasonic device 20, in turn, produces a electrical signal that can be used to determine the velocity, for example, of the blood flow constituents based upon the change in frequency of the re-radiated ultrasonic signal with respect to the ultrasonic signal transmitted by the second ultrasonic device 56, i.e., the Doppler shift. The relationship between the frequency of the transmitted ultrasonic signal and the frequency of the re-radiated ultrasonic signal detected by the ultrasonic device 20 is represented by the following equation.

$$f_d = v \cos(\phi) f_o / c \qquad (3)$$

where $f_o$ is the frequency of the transmitted ultrasonic signal, $f_d$ is the frequency of the received ultrasonic signal, "v" is the velocity of the blood flow constituent, "c" is the velocity of sound in the fluid of interest, which is blood in this case, $\phi$ is the difference in angle between the direction of motion of the blood flow constituent and the vector representing the direction in which the ultrasonic device 20 is sensitive.

Figure 8:
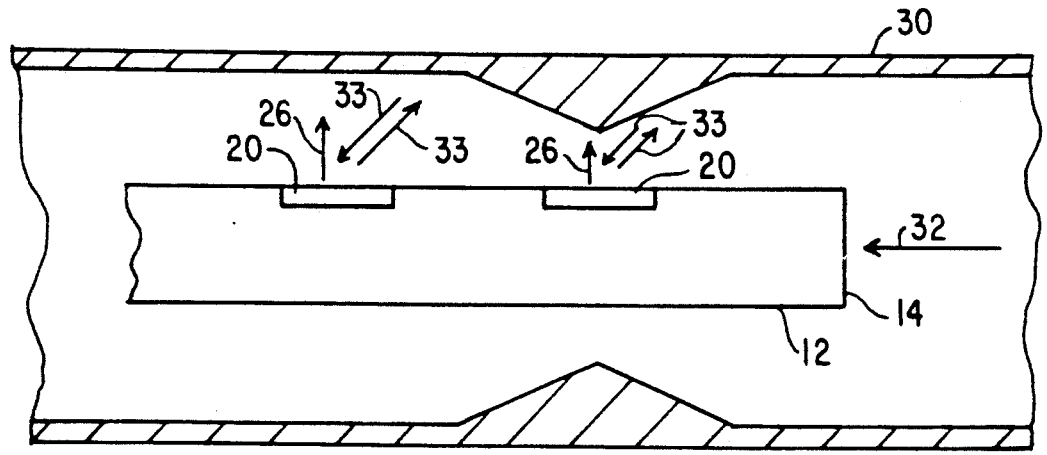
FIG. 8 illustrates an embodiment of the invention where two transducers that are separated from one another are used to locate a blockage or constriction in a blood vessel.

FIG. 8 illustrates a further embodiment of the apparatus 10 where two of the ultrasonic device 20 are employed to obtain ultrasonic information that can be used to construct a longitudinal blood velocity profile, for example. A longitudinal blood velocity profile, as shown in FIG. 7, can be used to locate a narrowing or constriction in the blood vessel based upon the difference in blood velocity between the portion of the blood vessel that is constricted and the portion of the blood vessel that is not constricted. The illustrated embodiment of the apparatus 10 employs flat plate versions of the ultrasonic device 20. However, two ultrasonic devices 20 that are shaped for conical beam sensitivity can, if necessary, be constructed and employed.

The foregoing description of the invention has been presented for purposes of illustration and description. Further, the description is not intended to limit the invention to the form disclosed herein. Consequently, variations and modifications commensurate with the above teachings and skill or knowledge of the relevant art are within the scope of the present invention. The preferred embodiment described hereinabove is further intended to explain the best mode known of practicing the invention and to enable others skilled in the art to utilize the invention in various embodiments and with the various modifications required by their particular applications or uses of the invention. It is intended that the pending claims be construed to include alternate embodiments to the extent permitted by the prior art.

What is claimed is:

1. An apparatus adapted for use in obtaining information relating to blood flow, comprising:
a carrier; and
diffraction grating means, operatively attached to said carrier, for use in transmitting a transmission wave that can be used to obtain information relating to the flow of blood in a blood vessel and that has a defined wavelength or receiving a reception wave that contains information relating to the flow of blood in a blood vessel and that has substantially said defined wavelength using the grating lobe effect, said diffraction grating means includes a member with a first surface and a second surface that is different than said first surface, a first electrode that is located on said first surface and a second electrode that is located on said second surface, wherein one of said first electrode and said second electrode includes a plurality of members that are substantially parallel to one another and spaced from one another by a defined distance, wherein the relationship between said defined wavelength and said defined distance is substantially in accordance with the Bragg diffraction equation.

2. An apparatus, as claimed in claim 1, wherein:
said carrier and said diffraction grating means are capable of being inserted into a blood vessel.

3. An apparatus, as claimed in claim 1, wherein:
said diffraction grating means includes a piezoelectric material.

4. An apparatus, as claimed in claim 1, wherein:
said diffraction grating means includes a piezoelectric material that is operative in a thickness mode.

5. An apparatus, as claimed in claim 1, wherein:
said member is made of a piezoelectric material and said first side is substantially parallel to, and separated from, said second side.

6. An apparatus, as claimed in claim 5, wherein:
said first electrode and said second electrode each includes a plurality of members that are substantially parallel to one another.

7. An apparatus, as claimed in claim 1, wherein: said diffraction grating means includes a surface that is exposed for substantially direct contact with a blood related structure through which said transmission wave or said reception wave will propagate.

* * * * *